United States Patent [19]

Lynch

[11] Patent Number: 4,934,368

[45] Date of Patent: Jun. 19, 1990

[54] MULTI-ELECTRODE NEUROLOGICAL STIMULATION APPARATUS

[75] Inventor: H. Wilfred Lynch, Racine, Wis.

[73] Assignee: MYO/Kinetics Systems, Inc., San Diego, Calif.

[21] Appl. No.: 146,454

[22] Filed: Jan. 21, 1988

[51] Int. Cl.$^5$ .............................................. A61N 1/00
[52] U.S. Cl. ............................ 128/419 R; 128/419 P; 128/419 N; 128/420.6; 361/331; 361/380
[58] Field of Search ............ 128/419 P, 420.6, 419 N, 128/419 R; 361/331, 380, 395

[56] References Cited

U.S. PATENT DOCUMENTS

| | | | |
|---|---|---|---|
| 3,881,495 | 5/1975 | Pannozzo et al. | 128/422 |
| 3,896,817 | 7/1975 | Hursen et al. | 128/419 R |
| 3,983,881 | 10/1976 | Wickham | 128/421 |
| 4,057,068 | 11/1977 | Comben | 128/419 P |
| 4,057,069 | 11/1977 | Dorffer et al. | 128/421 |
| 4,165,750 | 8/1979 | Aleev et al. | 128/422 |
| 4,232,679 | 11/1980 | Schulman | 128/419 PG |
| 4,314,562 | 2/1982 | Ware | 128/419 P |
| 4,392,496 | 7/1983 | Stanton | 128/423 |
| 4,421,336 | 12/1983 | Petrofsky et al. | 280/252 |
| 4,424,812 | 1/1984 | Lesnick | 128/419 PG |
| 4,492,233 | 1/1985 | Petrofsky et al. | 128/421 |
| 4,539,992 | 9/1985 | Calfee et al. | 128/419 PG |
| 4,539,993 | 9/1985 | Stanton | 128/421 |
| 4,545,381 | 10/1985 | Bournay et al. | 128/419 P |
| 4,592,359 | 6/1986 | Galbraith | 128/419 R |
| 4,785,827 | 11/1988 | Fischer | 128/420.6 |

FOREIGN PATENT DOCUMENTS 330342 9/1975 Australia .............................. 128/421

OTHER PUBLICATIONS

Proceedings of the 1st Vienna International Workshop on Functional Electrostimulation Basics, Technology and Application, Vienna, Austria, Oct. 19–22, 1983, Section 5.3—"Epineural Electrode Implantation for Electrically Induced Mobilization of Paraplegics" by J. Holle et al.
Section 5.4—"Functional Electrostimulation Makes Paraplegic Patients Walk Again" by H. Stoehr et al.
Section 5.7—"Intrafascilular Nerve Stimulation to Restore Locomotion in Paraplegics" by P. Rabischong et al.
Section 6.5—"Further Experiences with Elektrophrenic Respiration" by E. Moritz et al.
Section 8.1—"Multipolar Non Invasive Electrode for Partial, Direct Cyclic Skeletal Muscle Nerve Stimulation" by F. Ugolini.
Section 14.1—"The Role of Biomaterials Research for Electrical Stimulation" by H. Plenk, Jr.
Section 14.5—"Technology and Transcutaneous Supply of Implantable Electronic Stimulator Circuitry" by I. J. Hochmair-Desoyer et al.

Primary Examiner—Francis Jaworski
Assistant Examiner—George Manuel
Attorney, Agent, or Firm—Quarles & Brady

[57] ABSTRACT

An implantable system for Functional Electro-Stimulation (FES) is disclosed which includes an environmentally sealed implant case and a nerve cuff for attaching to the nerve. A plurality of leads connect the nerve cuffs to the case. The implant case provides redundant seals for entrance of the leads in a double wall/double environmental seal to provide long term sealing reliability for the case. Inside the case, the wires in each lead attach to connectors, which establish contact with an enclosed master circuitry case. The connectors allow the leads to be individually removed and replaced, thereby providing a maintainable system.

At the other end of the leads is attached the nerve cuff. Each nerve cuff has a hollow, gapped cylindrical shape, and includes electrodes on its inner surface. The cuff is deformable to allow placement around the nerve, holding the electrodes in electrical contact therewith.

In other embodiments of the invention, the nerve cuff includes a micro circuit which is capable of demultiplexing stimulation signals from a single pair of wires in the lead to drive multiple electrodes. These embodiments reduce the number of wires needed in each lead to facilitate the stimulation of a large number of nerves with a single implant.

6 Claims, 11 Drawing Sheets

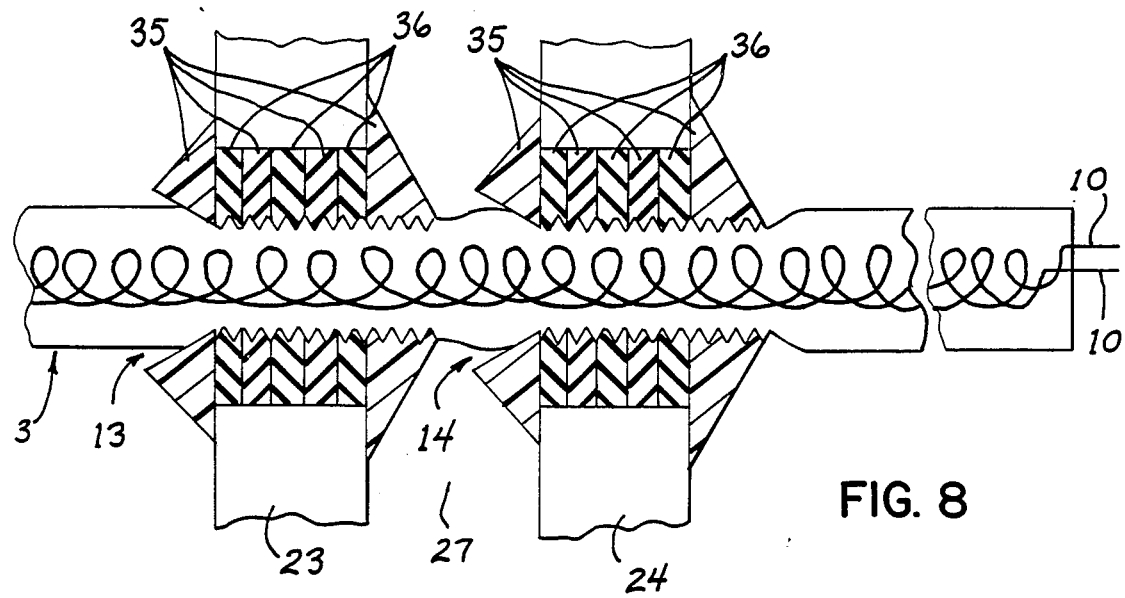
FIG. 8
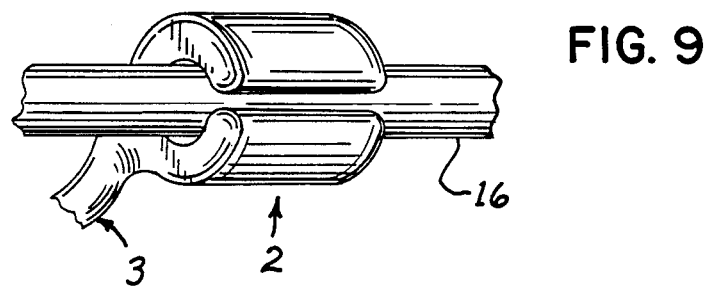
FIG. 9
FIG. 10
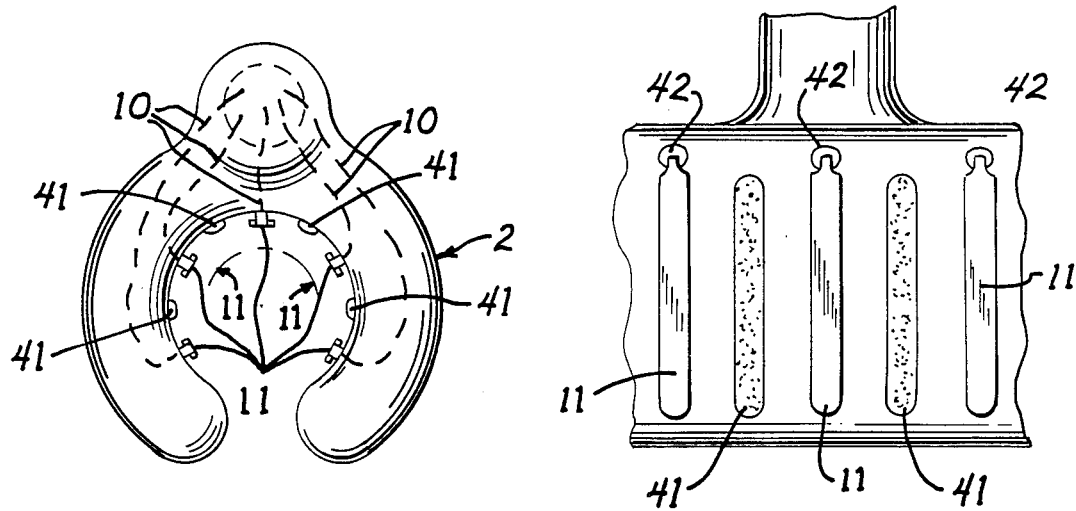
FIG. 11

NERVE CUFF MICRO CIRCUIT TIMING DIAGRAM

NERVE CUFF CONTROL
CIRCUIT STATE DIAGRAM

MULTI-ELECTRODE NEUROLOGICAL STIMULATION APPARATUS

BACKGROUND OF THE INVENTION

The field of the invention is neurological stimulators and, more particularly, implantable neurostimulators for use in Functional Electro Stimulation (FES) of skeletal muscles.

A great number of persons suffer from neurological disorders which render otherwise functional muscles usable due to the inability to naturally innervate the afflicted muscle groups. The most common forms of this malady are paraplegia and quadraplegia in which the normal nerve path to the muscle is interrupted, usually by spinal injury.

In such cases of paralysis, not only is the patient immobilized, but additionally, the muscles atrophy through time due to the lack of exercise. It is known, however, that artificial stimulation can be applied to skeletal muscles to prevent the deleterious effects of inactivity. Even further, research has been conducted, and is continuing, in the field of Functional Electro Stimulation (FES) in which the limited use of paralyzed members may be partially restored.

Many techniques are known for artificially stimulating nerves. The most common approach in FES is to use an implanted device which has one or more wires connected to the nerves to be stimulated. An external control unit transmits a coded Radio Frequency (RF) signal to the implant. The RF signal is coded with information to command the stimulation by the implant, for example, by supplying values for intensity, duration, and when to apply the stimulation.

The implant derives power from the RF signal and decodes it to extract the stimulation parameters. Batteries are therefore not needed and, in any event, would not be practical for this type of application since FES requires much more electrical power than, for example, a heart pacemaker which only triggers a self-sustaining nerve impulse.

In the simplest prior systems of this type, two wires are routed from the implant to each nerve to be innervated. At the attachment point on the nerve, a bare end of each wire is sutured onto the nerve. A current is then forced through the nerve between the attachment points of the two wires, thus stimulating the nerve.

It has recently been discovered that this type of "single-point" stimulation results in rapid fatigue of the stimulated muscle. The cause of the fatigue is that the nerve contains many separate areas of sensitivity which are responsible for simulating certain dedicated muscle fibers. By using single-point stimulation, the same muscle fibers are repeatedly stimulated and thus fatigue rapidly. It has further been discovered that when normal, undamaged nerves are stimulated naturally (e.g. by the brain), the stimulation is not confined to a single portion of the nerve, but rather "rotates" throughout the nerve during a single contraction. This "rotation" of the natural stimulation results in a variation of the muscle fibers being activated so that fatigue of a single muscle group is prevented.

As a result of this research, a system has been developed, as described in Austrian Pat. No. 330342, to replicate the above described natural rotation of stimulation by using several electrodes attached around the circumference of a nerve. The electrodes can then be energized in various combinations of polarity to produce many different zones of stimulation in the nerve. By cycling the electrode polarities, the stimulation is made to "rotate" in a more natural manner, preventing premature muscle fatigue This approach, however, requires approximately five electrodes per nerve, all of which must be connected to the implanted device. As a result, only a few nerves can be connected in this manner before the number of connections needed at the implanted device becomes prohibitive.

In an FES implant, it is desirable to stimulate a large number of muscles in order to replicate as nearly as possible natural movements. For example, to produce a natural gait, it is desirable to stimulate as many as 8 muscle groups in each leg. Prior implants were not able to accommodate the large number of connections that are needed for multiple nerve FES systems, especially when up to five electrodes are needed for each rotating stimulation electrode.

Further, prior implant cases were typically sealed units, which are unrepairable. Due to chemical effects to which the implant is subjected, splicing, etc. is not an acceptable practice for long term reliability. If a fault develops in one of the multiple leads or the implant electronics, the entire system must be replaced. This, of course, involves considerable surgery on the patient.

For similar reasons, the prior practice of suturing the electrodes onto the nerve has serious drawbacks. First, it is not possible to form a good seal between the wire and its surrounding insulation on the lead. This compromises the long term reliability of the lead. Secondly, the suture is a frail connection which may tear away from the nerve. That danger is complicated if rotating stimulation is to be used because each of the multiple electrodes would have to be sutured to the nerve in close proximity.

SUMMARY OF THE INVENTION

In one aspect of the present invention, an environmentally sealed case is provided for insuring long term reliability of the implant. The case includes a main body, within which is defined a main cavity for housing a master circuitry case. The master circuitry case contains the electronic circuits for generating stimulation pulses. The master circuitry case is connected to conductors, or wires, to carry the stimulation pulses to the nerves to be stimulated. The wires are embedded in leads which penetrate the case to route the wires to the applicable nerves.

In order to preserve the integrity of environmental seal, a case of this invention utilizes a double wall/double environmental seal at each point where a lead penetrates the case. A first wall is located on the outer periphery of the main body of the case. A second wall on the inside of the case defines an inner chamber bounded in part by the first and second walls. The inner chamber is closed with respect to both the main cavity of the case and the exterior of the case. The lead then enters the case by passing through the first wall, the inner chamber, and the second wall, into the main cavity.

First and second sealing means are provided on the first and second walls, respectively, to ensure an environmentally occlusive seal for the lead passing through the respective wall.

An important object of this invention is to provide an environmentally sealed case with enhanced long term reliability. The first and second sealing means, due to the presence of the inner cavity between them, provide redundant seals for the case. If the first sealing means should fail, the contamination could penetrate only as far as the inner cavity. The second sealing means would continue to prevent the entrance of contaminants into the main cavity.

The first and second sealing means of this invention may advantageously comprise alternating layers of dissimilar sealing materials. The differing materials may then be selected to each provide a different beneficial property to the sealing means. For example, one material may be selected for low moisture transfer, while the other is selected for long term compression retention. It is therefore an object of this invention to provide a sealing means which possesses both superior sealing integrity and long term sealing effectiveness.

In another aspect of this invention, a master circuitry case includes at least one conductive output pin for conducting an output signal out of the master circuitry case. The master circuitry case is held in a first case portion. A second case portion includes connector means associated with each output pin for establishing electrical connections. The connector means are arranged on an inner surface of the second case portion facing the master circuitry case and in registration with each associated output pin. The first and second case portions are mated to be releasably secured together, forming an environmental seal while joined but allowing for disassembly.

At least one lead enters the case, the lead containing at least one wire for conducting one of the output signals on one of the output pins to an attachment point at a nerve. The connector means is adapted to receive the wire, such that when the first and second case portions are brought together, each connector means mates with the associated output pin, forming electrical contact between the wires received by the connector means and the associated output pin.

Another object of the invention is to provide a case for neurological stimulator implants which allows maintainability of the implanted system. If, for example, a lead would become damaged and needed to be replaced, the connector means of this invention would allow replacement of the lead without replacing the entire implanted system. This is especially important in systems containing multiple leads. The first and second case portions may be separated, the damaged lead replaced by inserting the wires from the new lead into the connector means, and the case then reassembled to complete the repair.

Yet another object of this invention is to accommodate multiple outputs from the master circuitry case in order to stimulate a large number of different muscle groups, including multiple electrodes per group. This is accomplished in the present invention by including multiple output pins on the master circuitry case arranged in a predetermined pattern. Each corresponding connector means on the second case portion is then arranged in a mating pattern to complete the multiple connections.

Still another object of the invention is to provide a connector means as described above with improved long term reliability for the connection. This is accomplished in the present invention by a resilient pad means which has superior long term resiliency and which is arranged to urge each connector means into contact with the associated output pin.

In yet another aspect of the invention, a nerve cuff is provided for safely and reliably forming contact between an electrode and a nerve to be stimulated. The nerve cuff includes a lead from a stimulation source containing at least one wire. A main body of the nerve cuff is formed of a resilient material with a hollow center portion and a longitudinal gap open to the hollow center portion such that the main body is deformable to allow temporary enlargement of the hollow center portion for placement around the nerve. The main body is located on the end of the lead and forms an environmentally sealed termination for the lead.

The nerve cuff also includes at least one electrode on the inside surface of the cylindrical portion of the main body, facing the nerve. Transfer means are provided for coupling stimulation signals from each wire in the lead to each electrode. When the main body is placed around the nerve, each electrode is urged into contact with the nerve without damage.

An important advantage of the nerve cuff of the present invention is that sutures are no longer needed to attach electrodes to the nerve.

Another advantage of the nerve cuff of this invention is that the nerve cuff can be easily removed and replaced without trauma to the nerve.

In one implementation of the nerve cuff of the present invention, the lead includes one wire corresponding to each electrode and the transfer means comprises a direct connection of each wire in the lead to the corresponding electrode. In other words, the number of wires in the lead is equal to the number of electrodes. Each wire extends from the lead, through the interior of the main body, and attaches in electrical contact to the associated electrode.

The nerve cuff may also include multiple electrodes arranged around the circumference of the inner cylindrical surface of the main body. In that case, the stimulation pattern established by the electrodes can be varied to produce differing areas of stimulation in the nerve.

The accommodation of multiple electrodes is a particular advantage of this invention. Five or more electrodes are desired to achieve a natural, varying stimulation of the nerve. The nerve cuff is ideal for holding multiple electrodes in a desired pattern, with connections already established to wires in the lead.

In another implementation of the nerve cuff of this invention, the nerve cuff includes a plurality of electrodes and the transfer means includes micro circuit means. The micro circuit means provides for demultiplexing of stimulation signals so that a minimum number of wires may be used in the lead. The demultiplexed stimulation signals may then be applied to a plurality of electrodes via jumper means. This allows the use of a fewer number of wires in the lead than the number of electrodes.

A extremely important advantage of this invention is the reduction in the number of wires required in each lead while still allowing multiple electrodes to be used. Multiple electrodes allow the application of natural, varying stimulation as described above, but can not be readily accommodated by prior systems in which many nerves are to be stimulated because of the escalating number of connections required. By reducing the number of wires needed per nerve while maintaining a multi-electrode capability, the nerve cuff of this invention allows the practical implementation of more complex, multiple muscle group FES systems.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIG. 8 is a detailed cross-sectional view of the double wall/double environmental seal which forms a part of the case of FIGS. 3 and 4;

FIG. 9 is a detailed view of a nerve cuff which forms a part of the neurological stimulator apparatus of FIG. 1;

FIG. 10 is a top view of the nerve cuff of FIG. 9;

FIG. 11 is a circular sectional view taken on line 11—11 of FIG 10;

DESCRIPTION OF THE PREFERRED EMBODIMENT

Figure 1:
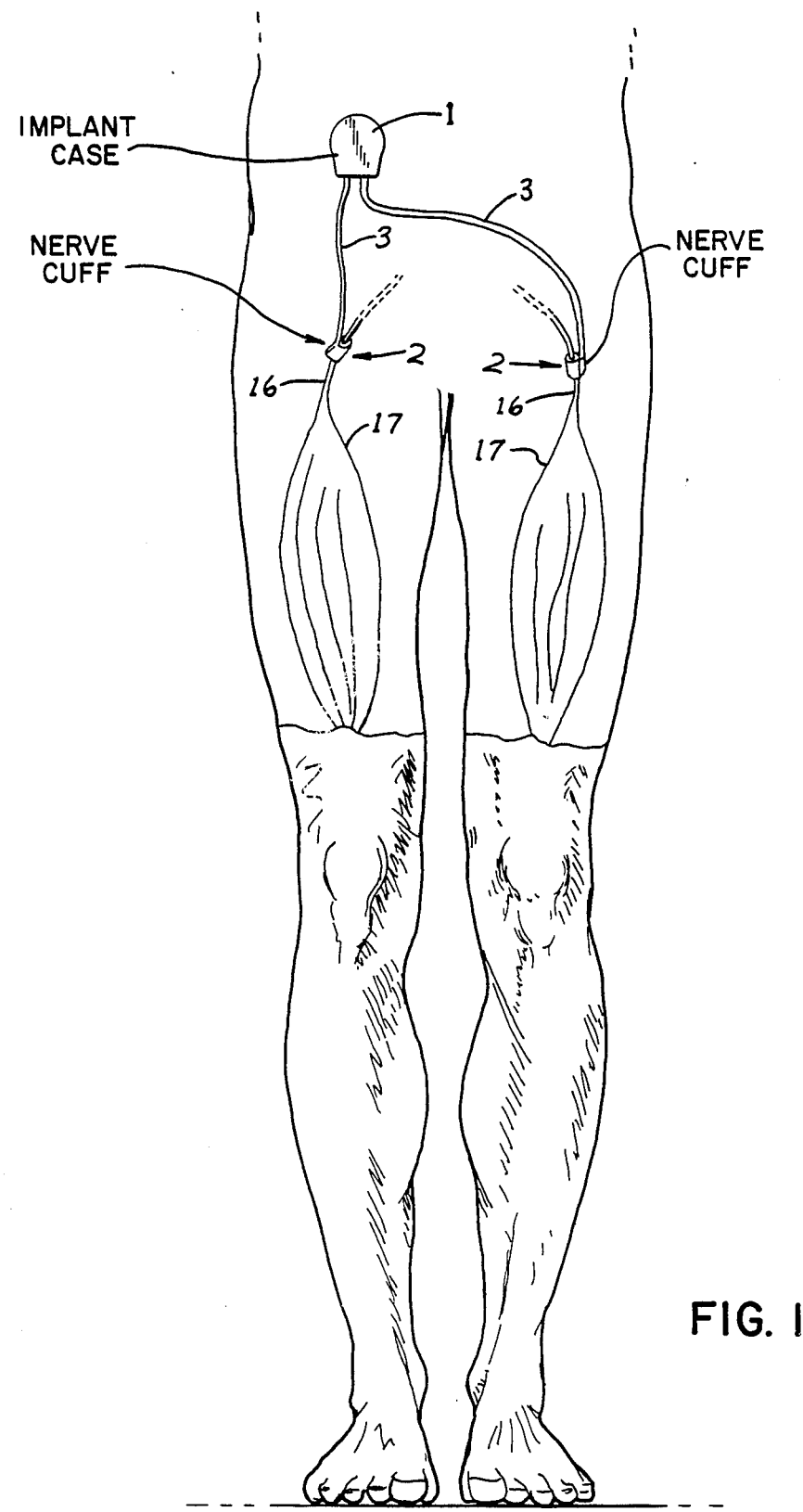
FIG. 1 is a pictorial view of a neurological stimulation apparatus of the present invention.

Referring to FIG. 1, a neurological simulation apparatus of the present invention includes an implant case 1 connected to nerve cuffs 2 by leads 3. As will be described below, the nerve cuff 2 provides an advantageous means for attaching electrodes to the nerve 16. In the example system of FIG. 1, each nerve cuff 2 is attached to the nerve 16 leading to the quadraceps muscle 17. The implant case 1 receives operating power and information signals by radio frequency (RF) coupling to an external unit (not shown in FIG. 1) as is well known in the art.

Figure 2:
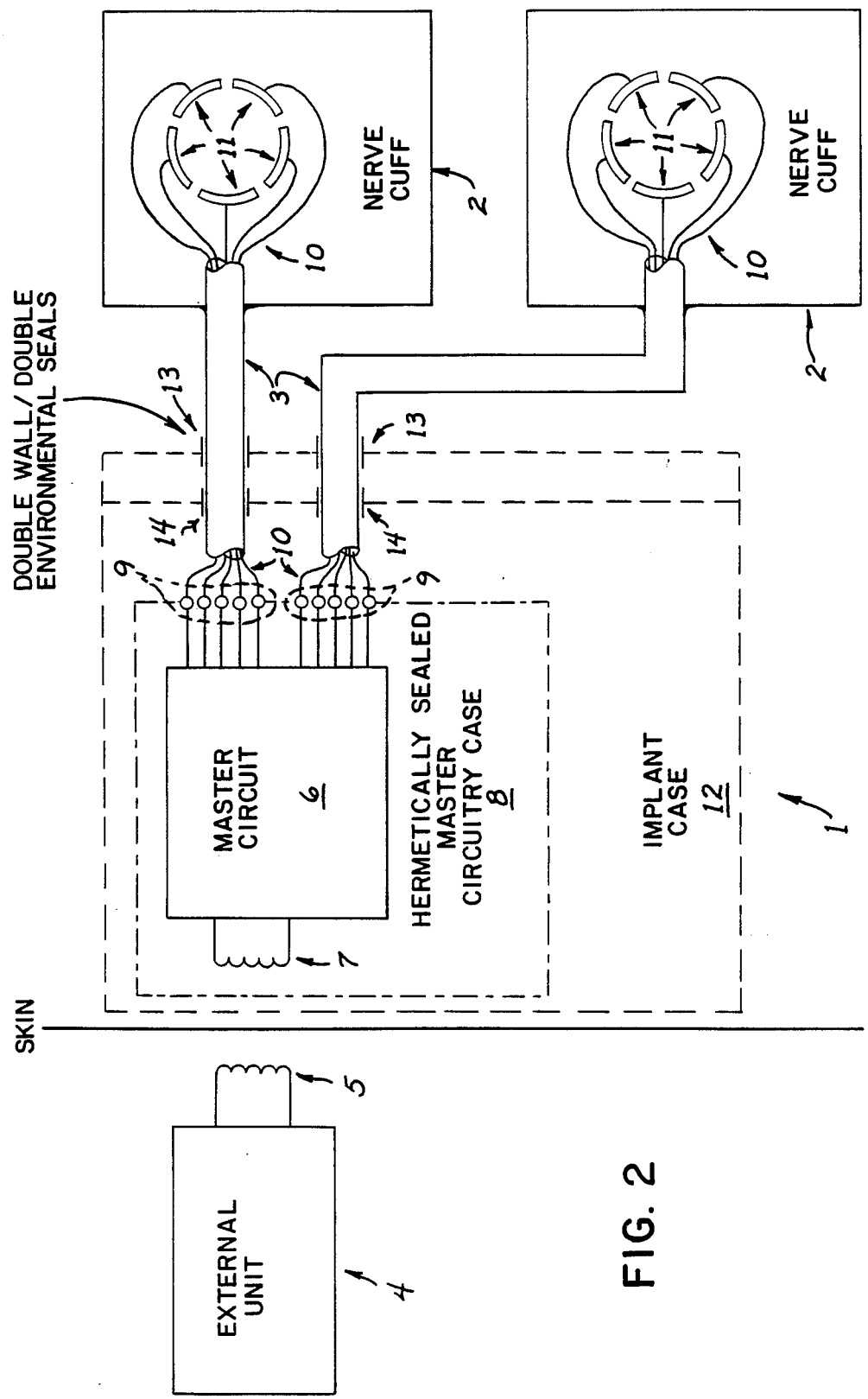
FIG. 2 is an electrical schematic diagram of the stimulation apparatus of FIG. 1.

Referring to FIG. 2, the external unit 4 transmits signaling information on a transmitting coil 5. The implant 1 includes a master circuit 6 which receives the transmissions from the external unit 4 on a receiving coil 7. The master circuit 6 is housed in a hermetically sealed master circuitry case 8 to protect the master circuit 6 from contamination. The master circuitry case 8 must be made of a nonconductive material, for example, glass or ceramic, to prevent shielding of the receiving coil 7.

The master circuit 6 derives both operating power and signaling information from the signal received from the external unit 4, as is well known in the art. The output of the master circuit 6 is presented on pins which mate with connectors 9. Each connector 9 allows connection of one wire 10 contained in the lead 3 to one of the pins on the master circuit 6. In this embodiment, there are two leads 3 with five wires 10 in each lead 3. Each lead 3 terminates in a nerve cuff 2, where each of the wires 10 connects to an electrode 11. The electrodes 11 are held in a circular arrangement in contact with the nerve by the novel nerve cuff structure which is described in detail below.

An important feature of this invention is long term reliability for the implant 1, accomplished by utilizing an implant case 12 to enclose the master circuitry case 8 and provide positive environmental protection for the termination of the leads 3 onto the master circuitry case 8. This is achieved by providing a double wall/double environmental seal for each lead 3, comprising an outer seal 13 and an inner seal 14, the structure of which is described in detail below.

Through the use of the environmentally sealed implant case 12 and the novel nerve cuff structure of this invention, functional electro-stimulation systems can be realized which are both highly reliable and simply attached.

Figure 3:
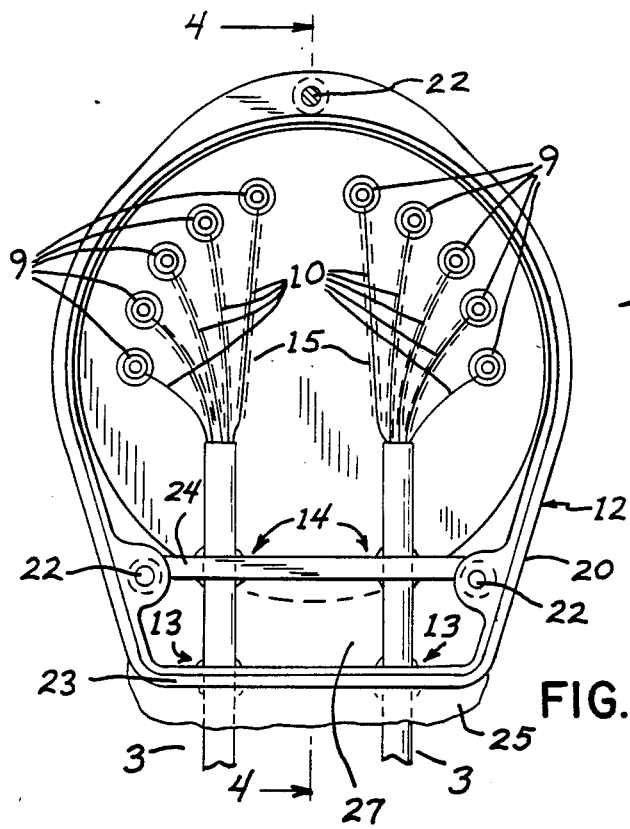
FIG. 3 is a top, exposed view of the implant case of the stimulation apparatus of FIG. 1.
Figure 4:
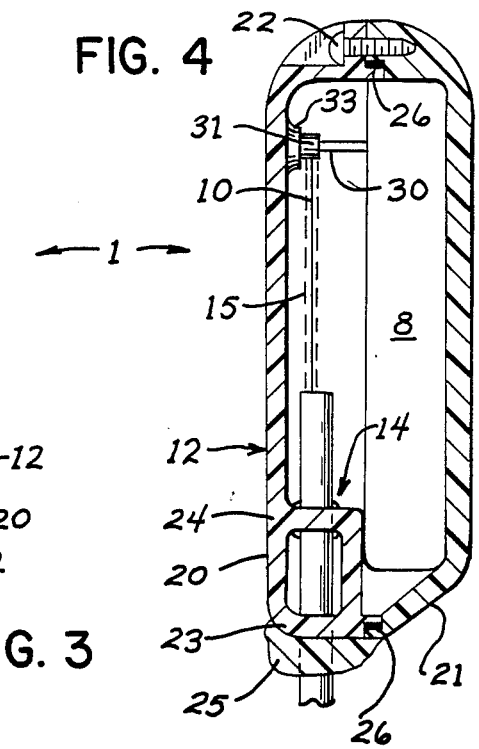
FIG. 4 is a sectional view taken along line 3—3 of FIG. 3.

Referring to FIGS. 3 and 4, the implant case 12 consists of a top half 20 and a bottom half 21. The two halves 20 and 21 are secured together by means of screws 22. When the two halves 20 and 21 are secured together, an edge seal 26 is formed which may comprise, for example, a sealing band or O-ring, to provide a positive seal between the case halves 20 and 21.

The penetration of the leads 3 into the case 12 are sealed by outer seals 13 and inner seals 14 which are described in detail below. The outer seal 13 is provided in an outer wall 23 of the case 12, while the inner seal 14 is provided in a inner wall 24. The two walls 23 and 24 are connected on both top and bottom to define an inner chamber, shown generally at 27, such that the seals 13 and 14 provide redundant protection against the entrance of contaminants into the case 12.

At the point where the leads 3 enter the case 12, a layer of soft silicone rubber 25 is applied to absorb any lateral strain on the leads 3. This layer of soft silicone 25 is applied after the case 12 and leads 3 have been assembled and can be removed, for example, by cutting, if a lead 3 needs to be replaced.

Each wire 10 in the leads 3 is routed to a connector 9, the structure of which is described in detail below. The wires 10 may be exposed either, for example, by chemical stripping, or the leads may be formed with the wires 10 already exposed. Because of the close spacing of the wires 10, short pieces of insulation, commonly referred to in the industry as "spaghetti" are placed around the wires 10 between the point where they leave the lead 3 and attached to their respective connectors 9.

Figure 5:
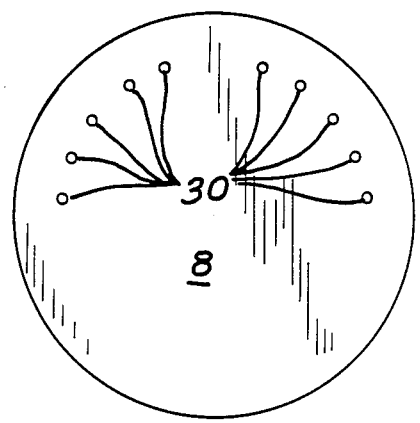
FIG. 5 is a top view of the master circuitry case which forms a part of the implant case of FIGS. 3 and 4.
Figure 6:
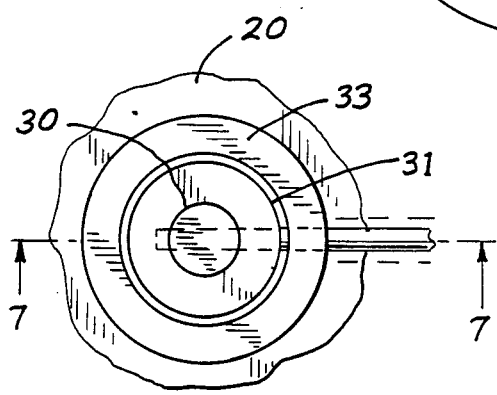
FIG. 6 is a detailed view of a connector which forms a part of the case of FIGS. 3 and 4.
Figure 7:
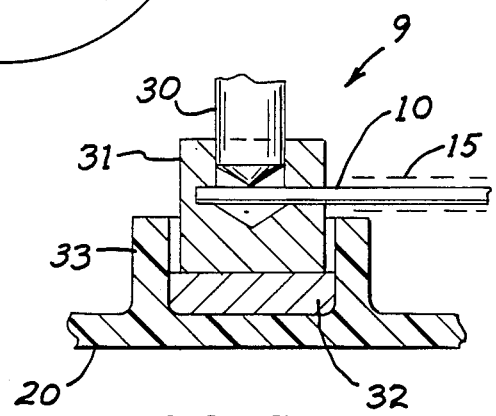
FIG. 7 is a sectional view taken on line 7—7 of FIG. 6.

Referring to FIGS. 5, 6, and 7, the detailed structure of the connectors 9, which is an important aspect of this invention, can now be described. The master circuitry case includes a set of output pins 30 spaced in a semicircle arc. The top half 20 of the case 12 includes a locating boss 33 registering with each of the pins 30 as the master circuitry case 8 in nested within the bottom half 21 of the case 12.

In each of the locating bosses 33, a sleeve 31 is mounted on a resilient pad 32. The sleeve 31 includes a top axial hole for the entrance of the pin 30 and an intersecting side bore for entrance of a wire 10. The connector 9 is shown in FIG. 7 just prior to complete assembly of the two halves 20 and 21. The pins 30 of each connector 9 are aligned in the sleeves 31 of each respective connector. The resilient pad 32 provides compliance for assisting in this alignment.

As the two halves 20 and 21 are pressed completely together, the pins 30 are urged further into the sleeves 31 making positive contact with the wire 10. The resilient pads 32 are compressed under the force of the pin 30 bottoming against the wire 10 in the sleeve 31. When the connector 9 is fully mated, the resilient pad 32 provides a constant pressure keeping the connector 9 tight over time.

The resilient pad 32 may either be a layer of silicone rubber or other mechanical means, for example, a wave spring. In this embodiment, a silicone rubber pad is preferred because the sleeve 31 may be advantageously secured to the pad 32 by adhesive to hold it captive.

Referring to FIG. 8, the details of the double wall-/double environmental seal provided b this invention is now described in detail. Each lead 3 in penetrating the implant case 12 passes through an outer seal 13 in the outer wall 23 and then through an inner seal 14 through the inner wall 24. Between the walls 23 and 24 is an inner chamber, shown generally as 27, which is closed with respect to the interior of the case 12.

If a fault should develop with any of the outer seals 13, contaminants would be admitted only as far as the inner chamber 27; the inner seals 14 would continue to function, preventing the entrance of the contaminants into the case 12. This double wall/double environmental protection is a highly desirable feature of this invention for providing long term reliability of the implant case 12, since the consequences of a failure in the case 12 are additional surgery and the attendant suffering by the patient.

While each of the seals 13 and 14 may be comprised of a homogeneous material, is it preferred in this embodiment that each seal be comprised of alternating layers of butyl rubber 35 and low compression set silicone rubber 36. Each of these materials 35 and 36 provides complimentary attributes for the seals 13 and 14; the butyl rubber providing exceptional moisture resistance, which the low compression set silicone rubber provides excellent long term retention of compressive properties.

The interior shaft of each seal 13 and 14 is formed with circular sawtooth ridges for gripping the lead 3 and for providing multiple barriers to penetration of contaminants. The lead 3 is made of a compressible silicone material and is drawn through the seals 13 and 14 during assembly. The wires 10 inside the lead 3 follow a helical path to prevent any strain on the wires 10.

The wires 10 preferred for this invention are made of a metal with the trade name "Elgiloy", a metal developed for use in watch springs by the Elgin Watch Company of Elgin, Ill. This material is preferred for its excellent long term resiliency and durability, which makes it especially suitable for use with the connectors 9.

Referring to FIGS. 9, 10, and 11, the details of the nerve cuff 2 of this invention are now presented. The cuff 2 itself has the general shape of a gapped hollow cylinder formed of a biologically acceptable polymer, for example, polyether sulfone. The cuff 2 is attached to the lead 3 at its terminus. The cuff 2 is applied to the nerve 16 simply by spreading the gap in the cuff 2, allowing it to be placed around the nerve 16, and then allowing the cuff 2 to relax to its normal, closed position.

The nerve cuff 2 of this invention thereby provides for a highly simplified attachment compared with the prior surgical procedure of suturing each electrode individually to the nerve 16. The cuff 2 may either be formed integrally with the lead 3 or formed separately and sealed to the lead 3, for example, by a final dip coat of silicone rubber with the electrodes masked.

The electrodes 11 are circumferentially spaced about the interior of the cuff 2. Each electrode 11 is a thin metal strip which penetrates the cuff 2 through a glass sealing bead 42. Each glass sealing bead 42 provides a positive seal between the cuff material and the electrode 11 to prevent entrance of contaminants.

Embedded in the interior of the cuff material, the wires 10 from the lead 3 are each extended and attached to one of the electrodes 11. As discussed above in the background of the invention, the circumferential positioning of the electrodes 11 is highly advantageous in that it allows the stimulation of many different portions of the nerve 16, thereby reducing muscle fatigue. The nerve cuff 2 of this invention is specifically adapted to achieve this result.

Once in place, the normal spring tension of the cuff may be relied upon to hold the electrodes 11 in contact with the nerve 16 However, it is additionally preferred in this embodiment that adhesive strips 41 be placed between the electrodes 11 on the interior of the cuff 2 in order to firmly secure the cuff 2 to the never 16. The material preferred for the adhesive strips is bysally adhesive which provides a strong, stretchy bond even in the presence of moisture.

Figure 12:
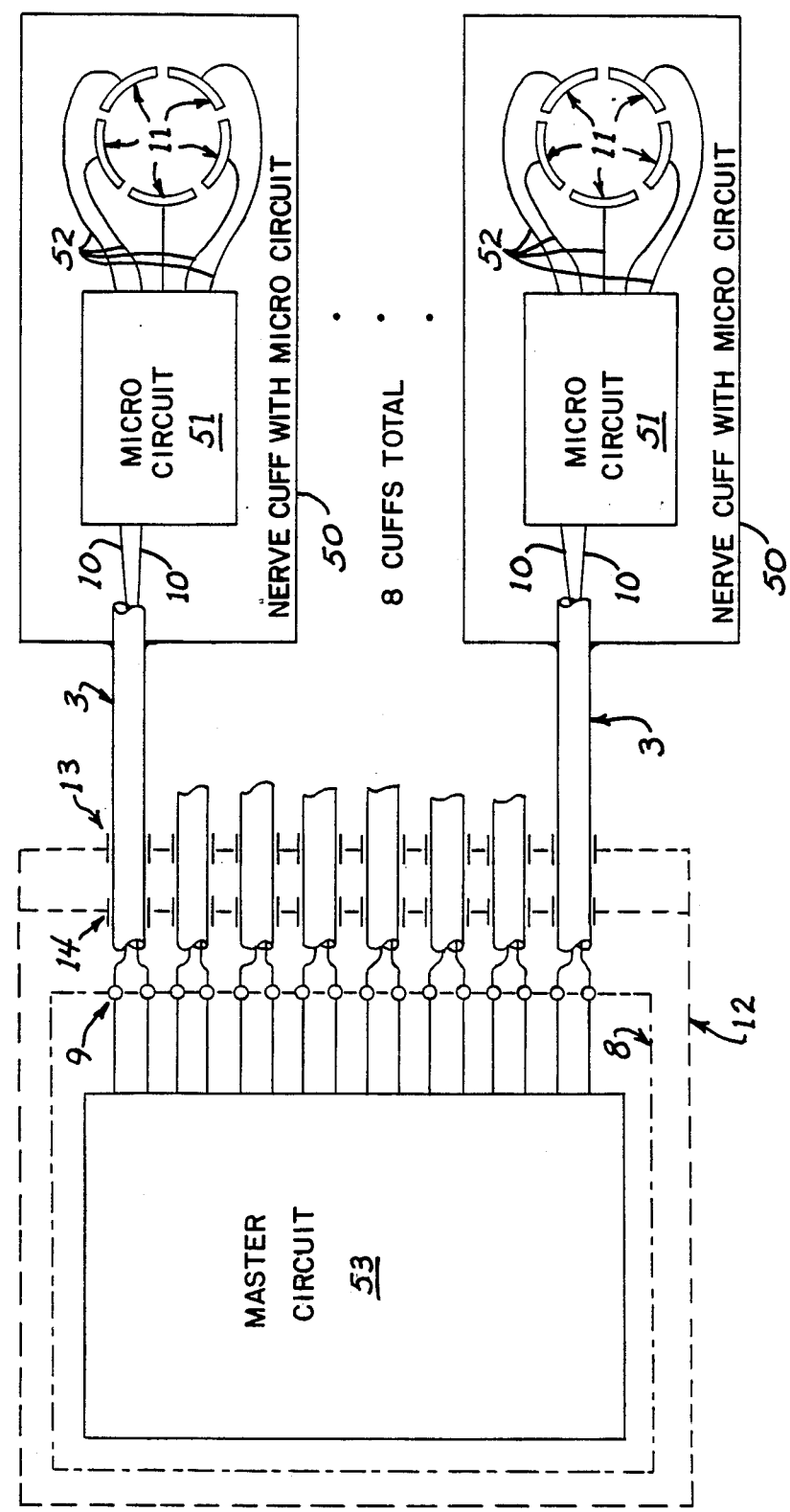
FIG. 12 is a schematic diagram of a second embodiment of the present invention.

Referring to FIG. 12, in other embodiments of this invention, each nerve cuff 50 may be advantageously provided with a microcircuit 51. As will be described in detail below, the microcircuit 51 performs an operation referred to herein as "demultiplexing", which allows a single pair of wires 10 to control the stimulation applied to all five electrodes 11. This reduces the number of wires required for each nerve from 5 to 2. This is an extremely important benefit of this invention, because it allows the stimulation of many more nerves, given a fixed connector capacity for the implant case 12.

The result of being able to stimulate a greater number of muscles is the achievement of a greater degree of natural movement in functional electro-stimulation. For example, to achieve a simulated four point gait in a paraplegic patient, it is necessary to control the stimulation of at least four muscles in each leg, at least eight muscles total.

In the embodiment of FIG. 12, this is accomplished using eight leads 3 with only two wires 10 and two connectors 9 per lead 3. A total of only sixteen connectors 9 are required in the implant case 12. It should be apparent that without the use of the microcircuit 51, forty connections would be required in the implant case 12 to achieve the same result, which would be extremely difficult or impossible to achieve.

Figure 13:
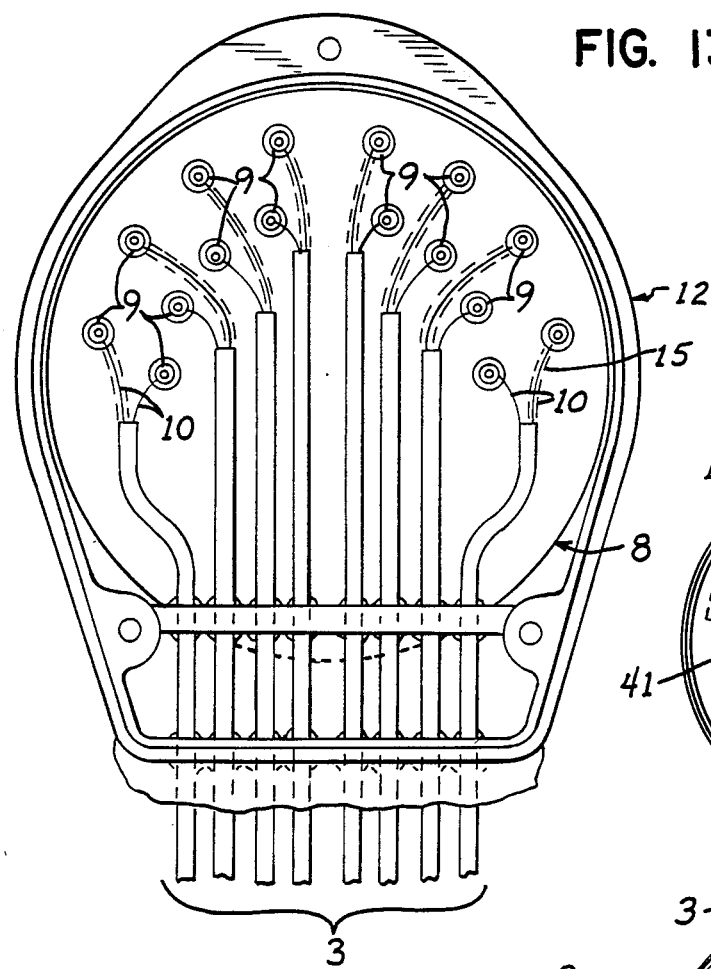
FIG. 13 is a top exposed view of the implant case which forms a part of the stimulation apparatus of FIG. 12.

Referring to FIG. 13, the implant case 12 in this embodiment is similar in structure to that of the first embodiment described above, in that it includes the same double wall/double environmental protection and connector structure 9. However, in this embodiment, eight leads 3 are provided, and the connectors 9 are staggered along separate arcs of differing radii. Each lead 3 contains two wires 10, one of which is protected by spaghetti 15 as described above.

Figure 14:
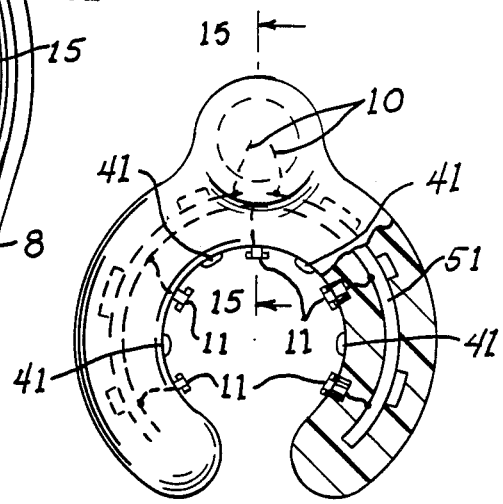
FIG. 14 is a top view of a nerve cuff which forms a part of the stimulation apparatus of FIG. 12.
Figure 15:
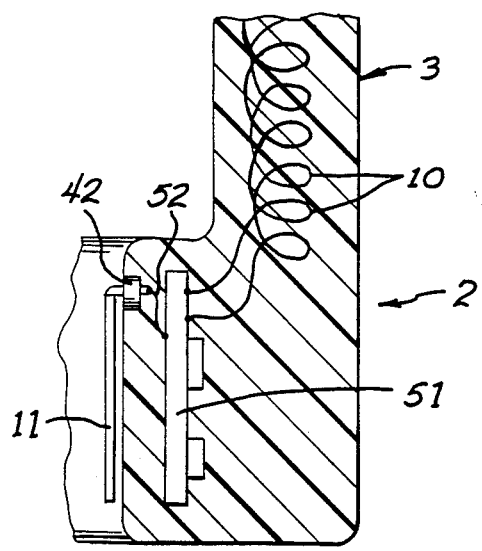
FIG. 15 is a sectional view taken along line 15—15 of FIG. 14.

Referring to FIGS. 14 and 15, in a second embodiment, the microcircuit 51 comprises a flexible film circuit 51 which is embedded inside the cuff 2. The two wires 10 from the lead 3 are attached onto the microcircuit 51. The microcircuit 51 also provides for the connection of a set of five output wires 52, each of which is attached to one of the electrodes 11. As described above, each electrode 11 passes through a glass sealing bead 42 before being connected to the jumper wires 52. Again, as described above, the nerve cuff 2 may include strips of adhesive 41 for securing the cuff 2 onto the nerve 16.

Figure 16:
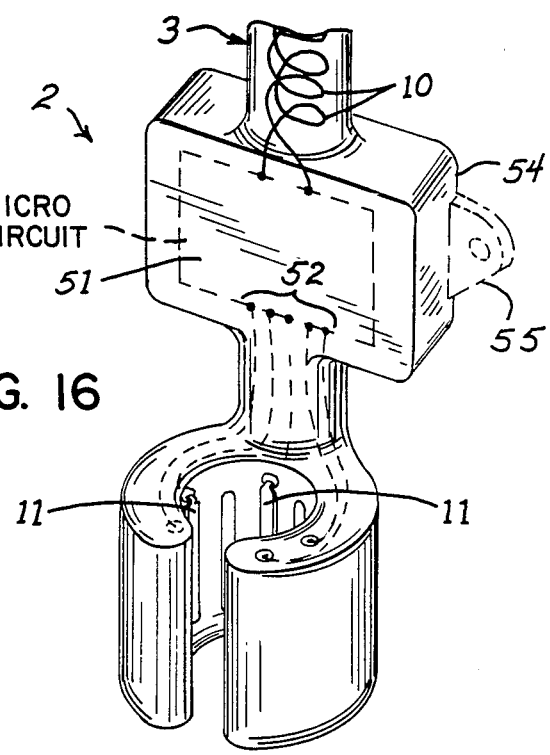
FIG. 16 is an alternate implementation of the nerve cuff of FIG. 14.

In a third embodiment shown in FIG. 16, the microcircuit 51 is contained in a nodule 54 pendent to the cylindrical portion of the cuff 2, which is otherwise as described above. The nodule 54 is integrally formed with the cylindrical portion of polyether sulfone material. The microcircuit 51 may either be a ridged or flexible film circuit contained in the interior of the nodule 54.

As with the other nerve cuff arrangement in the second embodiment described above, two input wires 10 and five jumper wires 52 attach to the microcircuit 51. The jumper wires 52 are then each connected to one of the electrodes 11.

In the embodiment of FIG. 16, a sewing tab 55 may optionally be provided to permit securing of the nodule 54 to tissue near the attachment point of the cuff 2.

Figure 17:
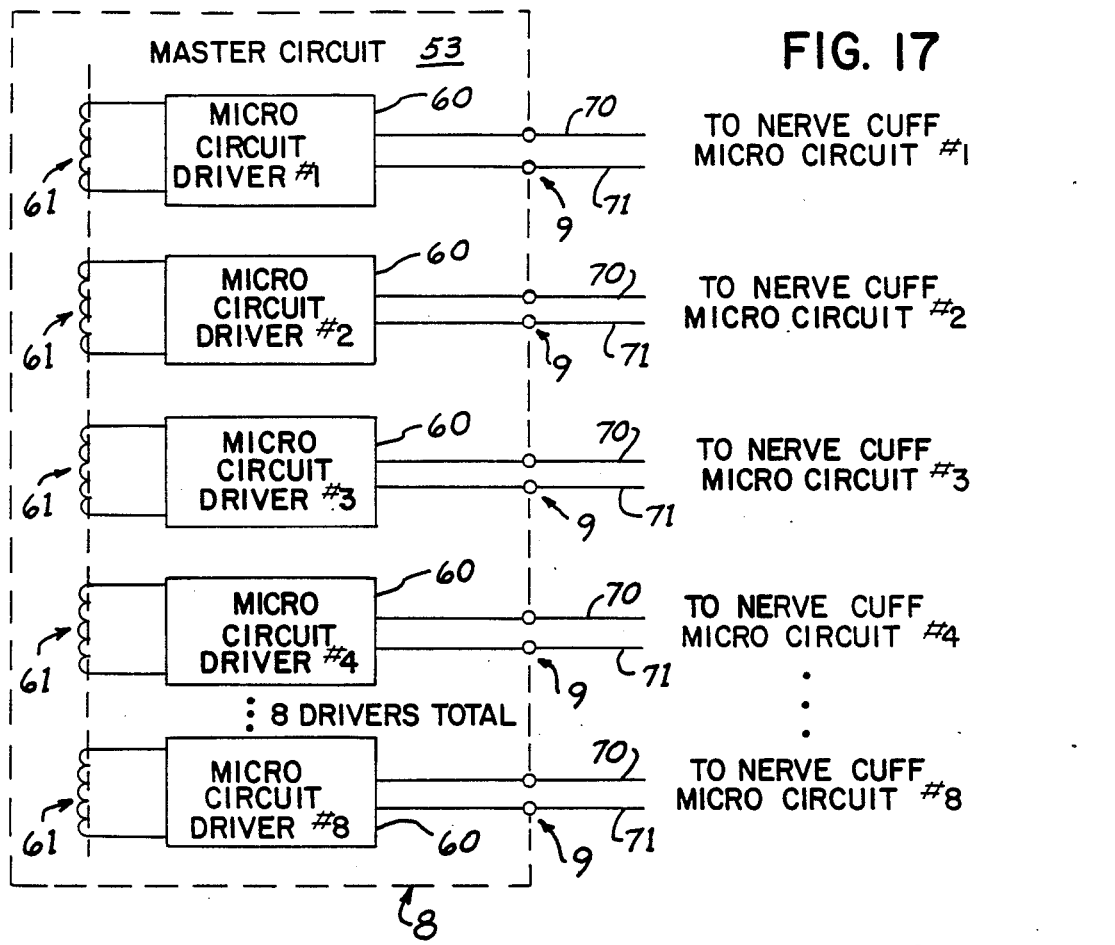
FIG. 17 is a schematic diagram of the master circuit which forms a part of the stimulation apparatus of FIG. 12.

Referring to FIG. 17, it will be understood that in the descriptions below, the nerve cuff 50 containing the microcircuit 51 may be either of the latter two embodiments. The master circuit 53 includes a separate microcircuit driver 60 for each nerve cuff 50 to be used. Each microcircuit driver 60 has its own separate RF receiving coil 61 so that all microcircuit drivers 60 are isolated from each other. In this embodiment, therefore, there are a total of eight microcircuit drivers 60 serving the eight nerve cuffs 50.

The output of each microcircuit driver 60 comprises two wires 70 and 71 which contain the stimulation signals, as described in detail below, which are demultiplexed by the microcircuit 51 to produce the stimulation on the multiple electrodes 11. Each wire 70 and 71 is connected to the master circuit 53 through connectors 9 which are the same as those described above in the first embodiment.

Figure 18:
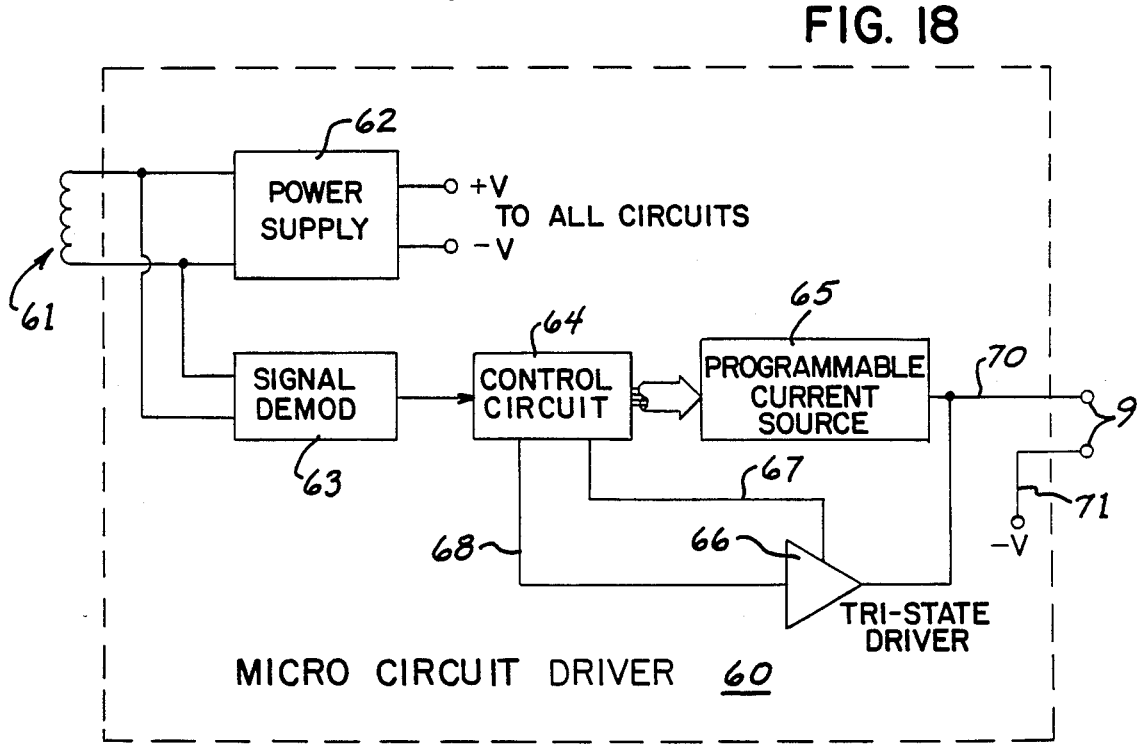
FIG. 18 is a block diagram of the microcircuit driver which forms a part of the master circuit of FIG. 17.

Referring to FIG. 18, the microcircuit driver 60 includes a power supply 62 attached to the receiving coil 61. The power supply 62 rectifies the RF signal received on the coil 61 to provide power for the operation of the associated microcircuit driver 60.

Each separate receiving coil 61 is arranged within the master circuitry case in a coaxial fashion, which is easily accomplished since each receiving coil 61 is only a few turns of small gauge wire. In this way, the supply voltages, $+V$ and $-V$, in all of the microcircuit drivers 60 are isolated from each other. This is important because of the presence of naturally occurring potential gradients in the body, between the various points where the nerve cuffs 50 will be attached.

By using isolated power supplies 62 for each microcircuit driver 60, the establishment of ground loops between nerve attachment points, and the presence of DC offset voltages between those same attachment points during stimulation, is eliminated. As will be discussed further below, it is therefore possible to eliminate the coupling capacitor characteristically used in prior implants of this type to alleviate such effects.

The output of the receiving coil 61 is also coupled to signal demodulator 63. The signal demodulator 63 extracts the coded information from the signal received from the external unit to determine the parameters of the stimulation pulse to be delivered. The stimulation parameters are coupled to a control circuit 64.

As will be described in detail below in relation to the microcircuit 51, each stimulation pulse cycle in this embodiment consists of first transmitting coded information to the microcircuit 51 to select the desired electrode polarities, followed by the actual stimulation pulse. The output lines 70 and 71 are therefore "multiplexed" between coded information and the actual stimulation pulse. The microcircuit 51 performs the reverse operation, i.e. "demultiplexing", by first extracting the coded information indicating which electrodes are selected, and secondly routing the actual stimulation pulse to the selected electrodes.

To transmit coded information to the microcircuit 51, the control circuit 64 enables a tri-state driver 66 via an enable line 67. The coded information is then presented to the tri-state driver 66 via input line 68. The output of the tri-state driver 66 is coupled to one of the output wires 70. The other output wire 71 is connected to the reference voltage source $-V$. During this signaling interval, when the tri-state driver is enabled, the signal on line 70 is driven with coded pulses of a constant amplitude.

After the signaling period is over, the control circuit 64 conditions a programmable current source 65 to generate the actual stimulation pulse over the same output line 70. The stimulation pulse has a variable voltage amplitude as required to produce the commanded stimulation current, and has a variable duration, also as commanded.

As mentioned above, prior stimulators of this type characteristically used a capacitor in the output of the stimulation current source. Such a capacitor is not utilized in this embodiment due to the isolation of the power supplies for the microcircuit driver 60.

However, the capacitors used in prior devices also function to limit the amount of current capable of being delivered to the nerve in case a hardware fault should develop in the implant. In this embodiment, since a coupling capacitor is not used, separate fault detection and current limiting circuitry can be used, as is well known in the art, to shutdown the microcircuit driver 60 in case of such faults.

Figure 19:
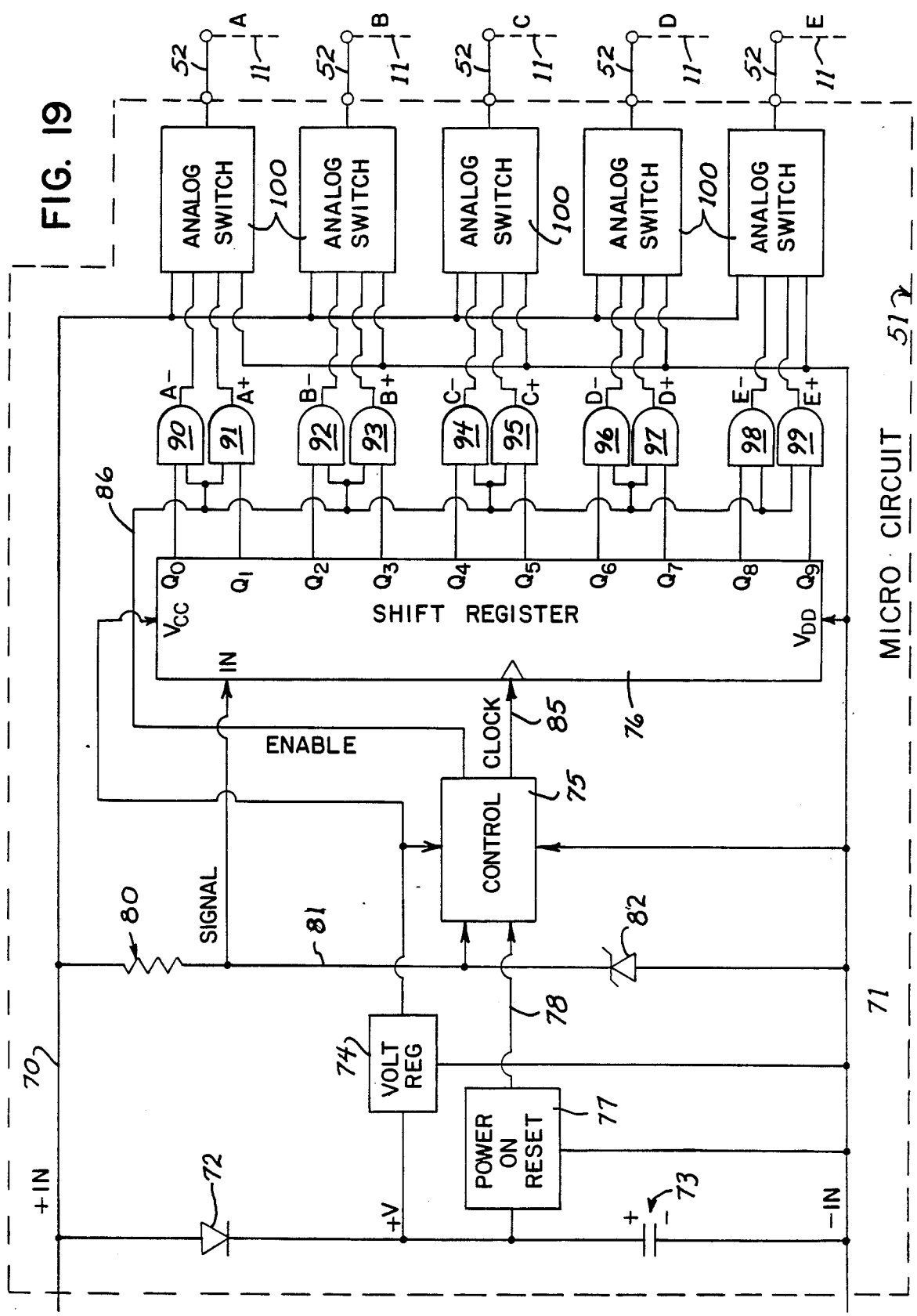
FIG. 19 is an electrical schematic diagram of the microcircuit which forms a part of the stimulation apparatus of FIG. 12.

Referring to FIG. 19, the operation of the microcircuit as follows. Line 71 is connected as a −IN signal, which is used as a ground reference. Line 70 is designated as +IN, and is used to provide both operating power and signaling information for the microcircuit 51.

The +IN signal 70 is connected to the anode of a diode 72. The cathode of diode 72 is connected to the positive terminal of a storage capacitor 73. As will be apparent from the discussion below, capacitor 73 need only be a very small value, so that miniaturization of the microcircuit 51 is enhanced.

Whenever the +IN signal 70 is high, either during signaling or during the actual stimulation pulse, capacitor 73 is charged. The voltage on capacitor 73 is applied to the input of a voltage regulator 74, which provides a regulated voltage for the operation of a control circuit 75 and a shift register at 76.

The +IN line 70 is also connected through resistor 80 to form a signal line 81. Signal line 81 is connected to the serial data input of shift register 76, and as an input to the control circuit 75.

While information is being sent to the microcircuit 51, the +IN signal is pulsed high and low. Signal line 81 follows these input pulses due to the blocking effect of diode 72 with respect to the supply voltage on capacitor 73. A zener diode 82 is provided to limit the voltage on signal line 81 to a logic "high" value. The logic circuits preferred for the microcircuit 51 are CMOS type due to their extremely low power consumption. The resistor 80 may therefore be a relatively large value so that negligible current is drawn during the actual stimulation pulse.

In general, data is transmitted to the microcircuit 51 and received on signal line 81. The control circuit 75 synchronizes to the incoming data and generates a pulse on a clock line 85 each time the signal line 81 is to be sampled for data. Clock line 85 is connected to the clock input of shift register 76, and for each clock pulse produced, the data on signal line 81 is shifted into the serial data input of shift register 76.

Shift register 76 presents the data shifted in as parallel outputs Q0–Q9. Outputs Q0 and Q1 are connected to one input of AND gates 90 and 91, respectively. The outputs Q0 and Q1 contain the polarity information for one of the electrodes 11, designated herein as electrode "A". If output Q0 is true, then electrode A is to be connected to the negative voltage −IN 71 during the actual stimulation pulse. If the output Q1 is true, then electrode A is to be connected to the positive input voltage, +IN 70. If neither output Q0 or Q1 is true, then the electrode A is to be left open, or floating.

Normally, outputs Q0 and Q1 should not both be true, as such an occurrence would simply short out the stimulation pulse, preventing it from being applied to any of the electrodes.

The other input of both AND gates 90 and 91 is connected to an enable signal 86 provided by control circuit 75. The enable line 86 is activated only after the control circuit 75 has detected that valid data has been received and is correctly aligned in the shift register 76. When that situation occurs, the enable line 86 is activated, and the outputs of AND gates 90 and 91 take on the respective values corresponding to outputs Q0 and Q1 to form the signals A− and A+.

The signals A− and A+ are then the polarity commands for electrode "A" indicating which supply voltage electrode A is to be connected to during the actual stimulation pulse. The polarity commands A− and A+, together with their associated supply voltages −IN and +IN, respectively, are applied to an analog switch circuit 100.

Similarly, shift register outputs Q2 and Q3 correspond to the polarities commanded for electrode "B", outputs Q4 and Q5 to electrode "C", and so on. The outputs of AND gates 92 and 93 are then the polarity commands B− and B+, respectively, and so on for all of the electrodes A–E. All of these polarity command are likewise applied to their respective analog switches 100.

Figure 22:
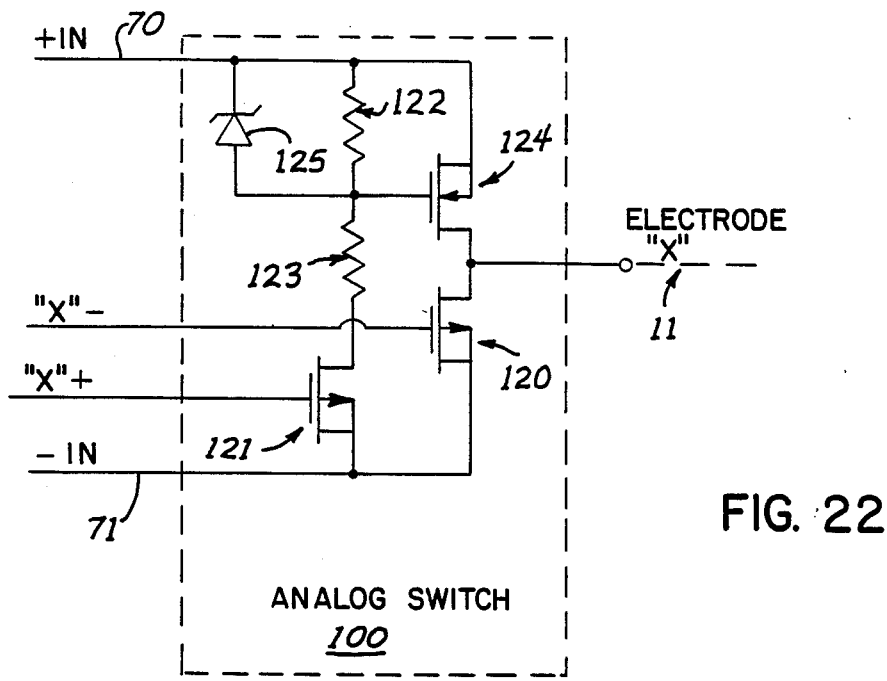
FIG. 22 is an electrical schematic diagram of the analog switch circuit which forms a part of the microcircuit of FIG. 19.

Referring to FIG. 22, the designation "X" is understood to represent the appropriate electrode (A−E) and the associated polarity commands. The negative polarity command signal X− is connected to the gate input of an N-channel MOSFET transistor 120. If the X− input is true, then transistor 120 is switched on, connecting the electrode X to the negative supply voltage −IN 71.

If on the other hand, the positive polarity command X+ is true, then N-channel MOSFET transistor 121 is switched on, which applies a signal through resistors 122 and 123 to the gate input of a P-channel MOSFET transistor 124. Transistor 124 is then likewise turned on, and serves to connect the electrode X to the positive supply voltage +IN 70. Zener diode 125 is provided in parallel with resistor 122 to limit the gate voltage applied to transistor 124 to a safe value.

Referring again to FIG. 19, AND gates 90-99 are used to gate the respective outputs Q0-9 with the enable signal 86, so that until the enable line 86 is made true, all of the polarity commands are false, leaving all of the electrodes in the open, or floating state.

When the enable signal is made true the polarity commands are applied to the analog switches 100, and the selected transistors are turned on. Then, when the actual stimulation pulse begins, the current is channeled with the desired polarity and to the desired electrodes according to the data just received. At the end of the stimulation pulse, the control circuit 75 is reset to begin accepting data for the next stimulation pulse.

Each stimulation cycle therefore receives new polarity command data to be shifted into the shift register 76, thereby allowing the stimulation pattern applied to the electrodes 11 to be varied in any arbitrary pattern. This achieves the rotating or natural stimulation, as described above, in successive stimulation cycles.

If stimulation cycles are repeated in rapid succession, the voltage on capacitor 73 will remain high allowing the micro circuit 51 to continue operating. During relaxation periods, when no stimulation cycles are being sent, the voltage on capacitor 73 will decay. When a new stimulation cycle is started, capacitor 73 will be again charged. A power on reset circuit 77 is connected to capacitor 73 and provides a reset signal 78 to the control circuit 75, indicating that the capacitor 73 has just been charged to a sufficient value.

Figure 23:
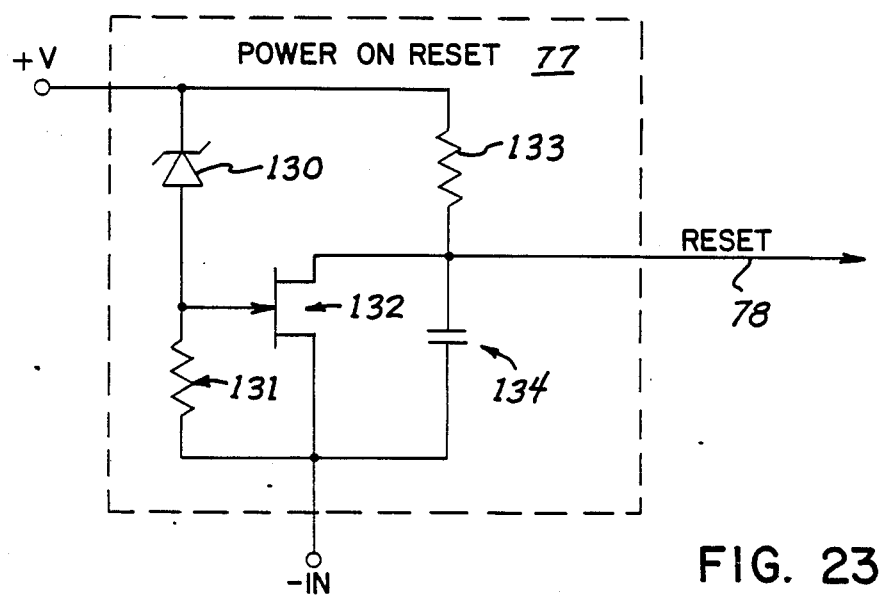
FIG. 23 is an electrical schematic diagram of the power on reset circuit which forms a part of the microcircuit of FIG. 19.

Referring to FIG. 23, the power on reset circuit applies the voltage on capacitor 73 to the gate input of a JFET transistor 132 through zener diode 130 and resistor 131. The JFET transistor 132 is normally in a conductive state, discharging capacitor 134 and holding the reset line 78 low. When the capacitor 73 voltage rises to a value sufficient to allow zener diode 130 to raise the voltage on the gate of transistor 132, transistor 132 will be cut off, allowing the reset signal 78 to rise, and initiate operation of the control circuit 75.

Figure 20:
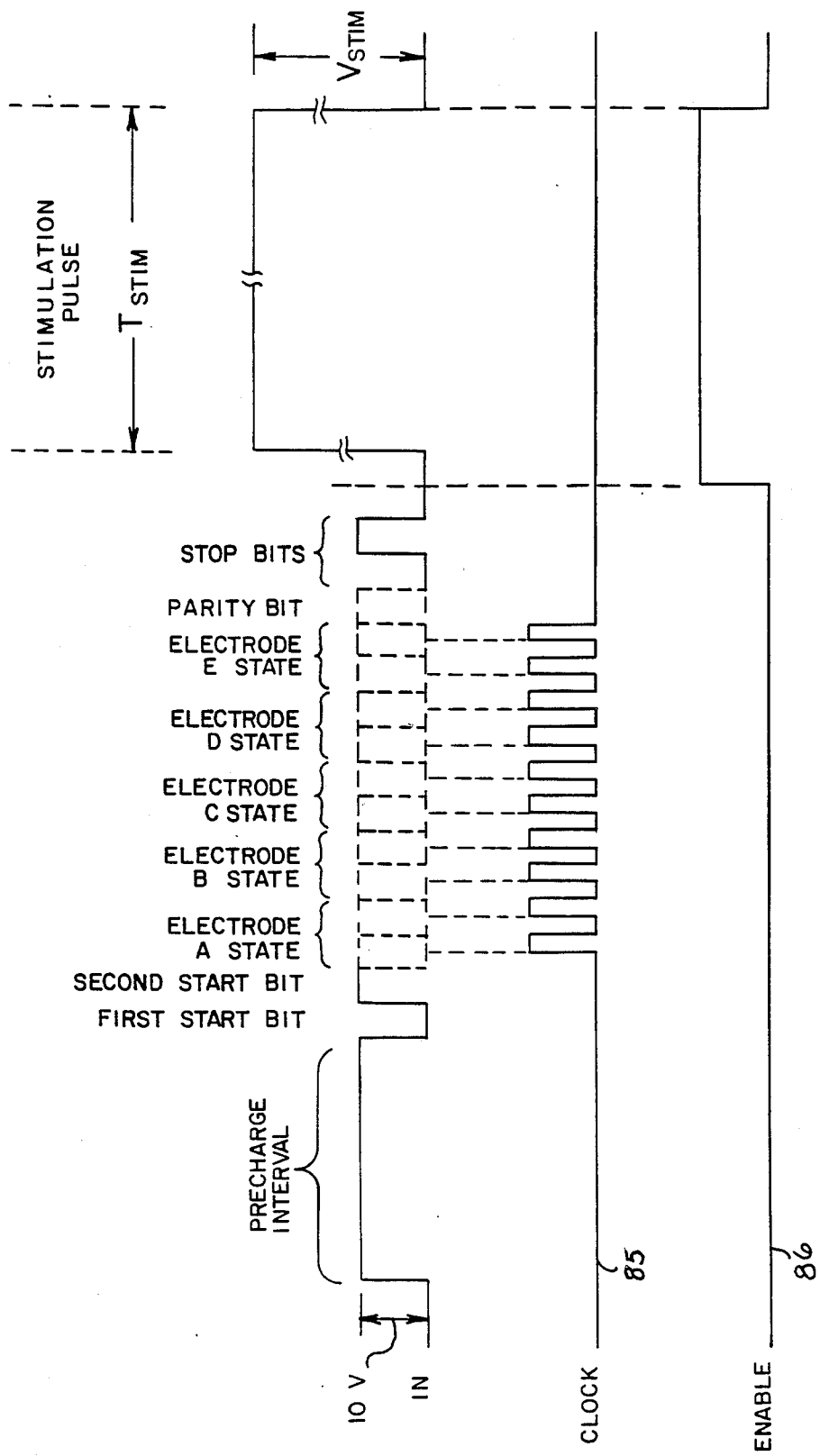
FIG. 20 is a timing diagram for a control circuit which forms a part of the microcircuit of FIG. 19.

Referring to FIGS. 18, 19, and 20, a stimulation cycle begins with the transmission of the polarity command data to the microcircuit 51. The data is transmitted by tri-state driver 66 as non-return to zero (NRZ) data with a pulse amplitude of approximately ten volts. It should be apparent to one skilled in the art that other coding schemes may be used, for example, manchester coding.

The data stream comprises an elongated precharge interval in which the capacitor 73 is charged up to a value allowing operation of the microcircuit 51. A first start bit follows the precharge interval, and always is a low voltage value. The first start bit is followed by a second start bit which is always a high voltage value. The falling edge of the first start bit is used as a reference to synchronize the control circuit 75 to the start of the data, while the width of the first start bit is used to indicate the width, or timing, of all the bits to follow.

After the second start bit, the next ten bits are data bits which contain the polarity commands for the five electrodes A through E. During this portion, the control circuit 75 produces a rising edge on the clock signal 85 at the midpoint of each bit period in the NRZ data stream, thereby clocking the incoming data into the shift register 76.

After all ten polarity commands have been received, a parity bit and two stop bits are received. The control circuit 75 verifies that the value of the parity bit results in even parity over the data and parity bits. If not, then a parity error has occurred and the enable signal 86 is not activated, preventing the stimulation pulse from being applied during this stimulation cycle.

After the parity bit, two stop bits are received, the first stop bit being always low and the second stop bit always being high. If these two stop bits are not received in the correct order and at the correct time, then a framing error has occurred and the control circuit 75 likewise prevents activation of the enable signal 86, suppressing the stimulation pulse for this stimulation cycle.

If none of these errors has occurred, the enable signal 86 is made true approximately one bit period after the end of the last stop bit. At that time, the control circuit 64 in the microcircuit driver 60 deactivates the tri-state driver 66. Approximately one bit period thereafter, the microcircuit driver 60 actives the programmable current source 65 to deliver the actual stimulation pulse.

The magnitude of the voltage delivered by programmable current source 65 is designated as $V_{STIM}$, and has a variable height depending on the magnitude of the desired stimulation pulse. Similarly, the duration of the stimulation pulse, designated as TSTIM, is variable according to the commanded duration of the stimulation pulse. The stimulation pulse is controlled entirely by the control circuit 64 in the microcircuit driver 60, both in magnitude and duration.

The stimulation pulse ends when the control circuit 64 commands the output of the programmable current source 65 to zero. Control circuit 75 in the microcircuit 51 detects that falling edge of the stimulation pulse, and in response thereto resets the enable line 86 false. At that point, the control circuit 75 in the microcircuit 51 is reset to except another stimulation cycle.

It should be noted that there will be at least two polarity commands high during the signalling interval which will keep capacitor 73 charged. Inverted logic may be used so that "off" polarity commands are a high voltage value, further enhancing retention of charge on capacitor 73. A high data rate, for example, 9600 BAUD, is likewise preferred to minimize the size required for capacitor 73. Capacitor 73 therefore only needs to supply power for a few bit periods. In any event, capacitor 73 must be kept to a small value so as not to interfere substantially with the stimulation pulse.

Figure 21:
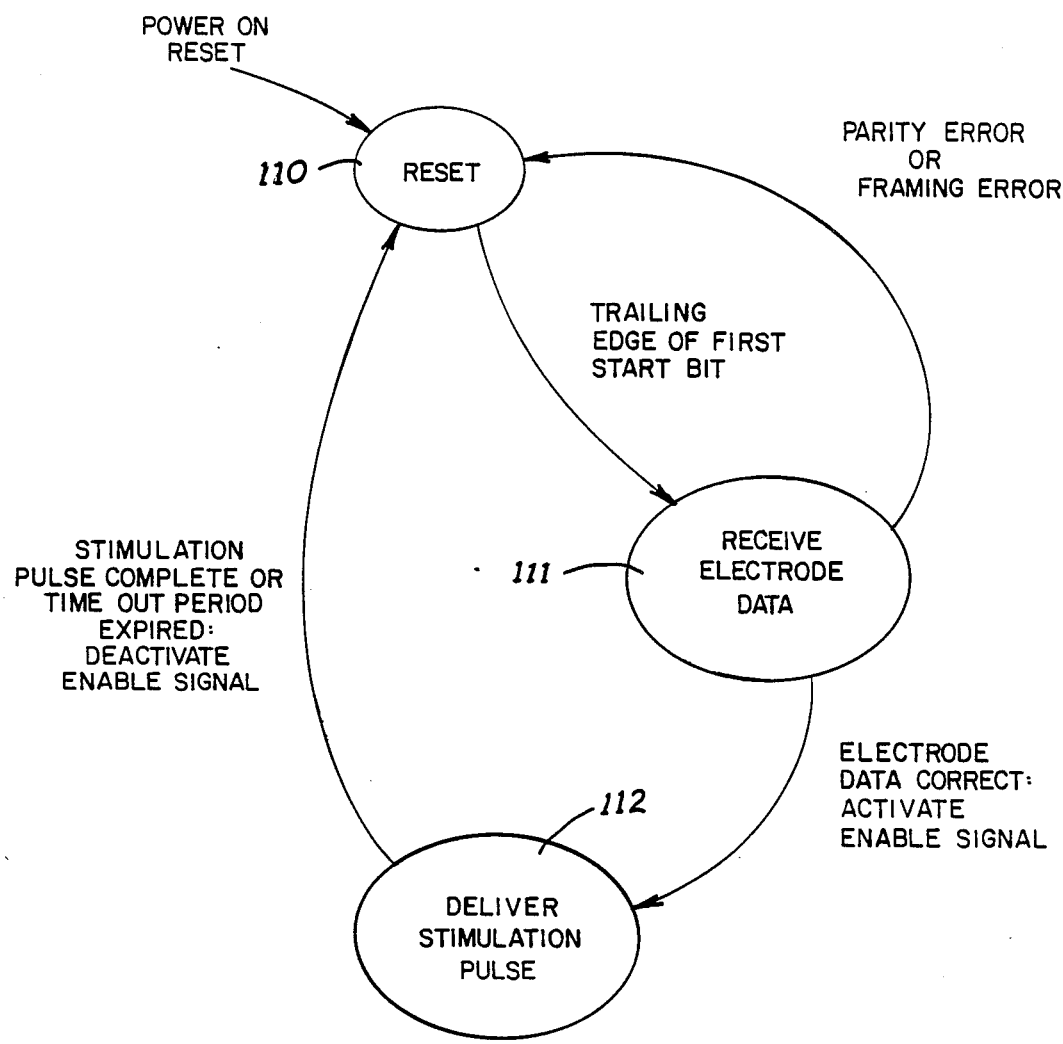
FIG. 21 is a state diagram of the control circuit which forms a part of the microcircuit of FIG. 19.

Referring to FIG. 21, the operation of the control circuit 75 in the microcircuit 51 is represented in state diagram form. Upon receiving a reset signal from the power on reset circuit 77, the control circuit 75 enters a "reset" state 110. In the "reset" state 110, the control circuit 75 has power applied from the elongated precharge interval. The first and second start bits are received in the "reset" state, and the first start bit is used to synchronize the control circuit 75 to the incoming data stream.

When the trailing edge of the second start bit is detected, the control circuit 75 enters a "receive electrode data" state 111. In the "receive electrode data" state 111 pulses are produced on the clock line 85 to clock the electrode polarity command bits into the shift register 76. Upon completion of the polarity command bits, the parity bit and stop bits are checked, as described above, to detect a parity or framing error, respectively.

If either such error is detected, the "reset" state 110 is immediately reentered without activating the enable signal 86. This could occur, for example, if synchronization is lost between the microcircuit 51 and the microcircuit driver 60 resulting in a stimulation pulse being mistaken for an information transmission. In that case, both a parity error and framing error will be detected, and the cycle will repeat until a valid information transmission is received.

In the "receive electrode data" state 111, if all of the data is correctly received, the control circuit 75 enters a "deliver stimulation pulse" state 112 and the enable signal 86 is activated. In the "deliver stimulation pulse" state 112, the control circuit 75 monitors for a rising edge on signal line 81, followed by a falling edge on signal line 81, indicating the completion of a stimulation pulse.

If the stimulation pulse does not begin within approximately two bit periods after the enable signal 86 is activated, a time out error is generated; the control circuit 75 immediately deactivates the enable signal 86 and reenters the "reset" state 110.

If, on the other hand, the start of the stimulation pulse is detected normally, the enable signal 86 remains high and the stimulation pulse is allowed to continue until its termination by the microcircuit driver 60. Upon detecting the falling edge of the stimulation pulse, the control circuit 75 enters the "reset" state 110 awaiting reception of the next stimulation cycle.

There has been described above several preferred embodiments of the invention. It should be apparent to one skilled in the art that other embodiments equivalent to those described are also envisioned by this invention. For example, the microcircuit described uses two input wires and alternately receives polarity commands and stimulation pulses. If desired, three input wires could be used, allowing polarity commands and stimulation pulses to be received simultaneously at the expense of an additional wire. In that case, a separate signal wire could be advantageously used to supply constant power and information data to the microcircuit by modulating, or multiplexing, the information data onto the normally high separate signal wire. This alternate approach is useful if the time needed to transmit the polarity data between stimulation pulses is prohibitive for a particular application.

I claim:

1. A case for an implanted neurological stimulator comprising:
   a main body having an exterior surface enclosing an interior volume;
   a first wall subdividing the interior volume of the main body to form a main cavity and an inner chamber;
   a second wall formed on the exterior surface of the main body, the second wall bounding at least a portion of the inner chamber;
   a master circuitry case arranged within the main cavity;
   at least one continuous lead connected to the master circuitry case in the main cavity and extending continuously from the main cavity to an area outside of the main body by making a first penetration through the first wall from the main cavity to the inner chamber and a second penetration through the second wall from the inner chamber to the area outside of the main body;
   at least one first sealing means formed on the first wall for providing an environmentally occlusive seal for the first penetration of each lead through the first wall; and
   at least one second sealing means formed on the second wall for providing an environmentally occlusive seal for the second penetration of each lead through the second wall.

2. The case of claim 1 in which the first and second sealing means each comprises alternating layers of at least two dissimilar sealing materials.

3. An implant case for a neurological stimulator comprising:
   a master circuitry case;
   at least one conductive output pin on the master circuitry case;
   a first case portion adapted to receive the master circuitry case;
   a second case portion mated to the first case portion;
   means for releasably securing the first and second case portions together;
   at least one lead entering the second case portion, each lead containing at least one wire, each wire having a first end adapted for attachment to a nerve;
   connector means associated with each output pin on the master circuitry case, each connector means being located on an inner side of the second case portion facing the master circuitry case in the first case portion, and each connector means being adapted to receive a second end of one of said wires for connection to the master circuitry case, such that when the first and second case portions are secured together, each output pin mates with the associated connector means, forming electrical contact between each output pin and the second end of the wire received by the associated connector means.

4. The case of claim 3 in which said at least one conductive output pin on the master circuitry case comprises a plurality of conductive output pins arranged in a fixed, predetermined pattern and a plurality of connector means are arranged in a mating pattern.

5. The case of claims 3 or 4 in which the connector means comprises;
   a locating boss formed on the inner side of the second case portion;
   resilient pad means arranged in the locating boss; and
   a sleeve formed from a conductive material and located on the resilient pad means in the locating boss, the sleeve including an axial bore to accept the output pin with which the connector means is associated and a radial bore to accept the second end of the wire which is received by the connector means, the radial bore intersecting with the axial bore;
   wherein when the first and second case portions are secured together the output pin with which the connector means is associated is inserted into the axial bore and is forced into contact with the wire in the radial bore, forcing the sleeve to deform the resilient pad means such that the resilient pad means maintains a restorative force urging the sleeve against the output pin inserted therein.

6. The case of claim 5 in which the resilient pad means comprises a layer of silicone rubber and the sleeve is fastened to the resilient pad with adhesive.

* * * * *